United States Patent [19]

Green

[11] 4,312,992
[45] Jan. 26, 1982

[54] SUBSTITUTED HETEROFULVALENES

[75] Inventor: Dennis C. Green, Hopewell Junction, N.Y.

[73] Assignee: International Business Machines Corporation, Armonk, N.Y.

[21] Appl. No.: 74,927

[22] Filed: Sep. 13, 1979

Related U.S. Application Data

[63] Continuation-in-part of Ser. No. 747,136, Dec. 3, 1976, abandoned.

[51] Int. Cl.³ .................. C07D 339/06; C07D 343/00; C07D 345/00
[52] U.S. Cl. ............................... 549/59; 260/239 R; 549/35; 549/39
[58] Field of Search ...................... 260/239 R; 549/59

[56] References Cited

PUBLICATIONS

Narita et al. "Synthesis" No. 8, vol. 1, pp. 489–514 (1976).

*Primary Examiner*—Donald G. Daus
*Assistant Examiner*—D. B. Springer
*Attorney, Agent, or Firm*—Hansel L. McGee

[57] ABSTRACT

Substituted derivatives of tetrathiafulvalene, tetraselenafulvalene and dithiadiselenafulvalene having the general formulae

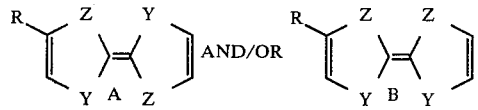

where Z is S and Y is S; Z is S and Y is Se; and Z is Se and Y is Se, and R can be $CO_2H$, $R'R''COH$, $R'CHOH$, $COR'$, $SCH_3$, $SO_2^-Li^+$, $SnR_3'$, $SiR_3$, $-CH_2OH$ $-CO_2R'$, $R'CHOH$, $CHO$, $CR_2'$ $CR_2'OH$, TTF, TSeF and DTDSeF, R' and R'' can be the same or different and is selected from the group consisting of alkyls, aryls, alkaryls, ether substituted alkyls, halogen substituted alkyls and halogens, are prepared. A novel method for their preparation is also described.

15 Claims, No Drawings

SUBSTITUTED HETEROFULVALENES

The government has rights in this invention pursuant to Contract No. DAAG-29-75-C-0010 awarded by the U.S. Army Research Department.

CROSS-REFERENCE TO RELATED APPLICATION

This application is a continuation-in-part of application Ser. No. 747,136, filed Dec. 3, 1976, now abandoned, entitled SUBSTITUTED HETEROFULVALENES, which is assigned to the same assignee as the present invention.

BACKGROUND OF THE INVENTION

1. Field of the Invention

The invention relates to the novel synthesis of novel substituted derivatives of tetrathiafulvalene, tetraselenafulvalene and dithiadiselenafulvalene and their conducting charge transfer salts with tetracyano-p-quinodimethane.

2. Prior Art

Considerable interest has been found recently in the study of highly conducting organic charge transfer salts. Most attractive of these systems are the tetracyano-p-quinodimethane (TCNQ) salts of tetrathiafulvalene (TTF), tetraselenafulvalene (TSeF) and dithiadiselenafulvalene (DTDSeF). These salts display exceptional electrical conductivity and metallic behavior over a wide temperature range.

Presently, interest has been focused on substituted derivatives of the tetraheterofulvalenes, where hetero means S and/or Se which are hereafter referred to as fulvalenes. Substituted fulvalenes are of interest because they alter the conductivity of their charge transfer salts.

Prior attempts to synthesize unsymmetrically substituted fulvalenes have been by a cross coupling reaction described by M. Narita and C. Pittman, Jr. *Synthesis,* 1976, 495. The reaction can be generalized as follows:

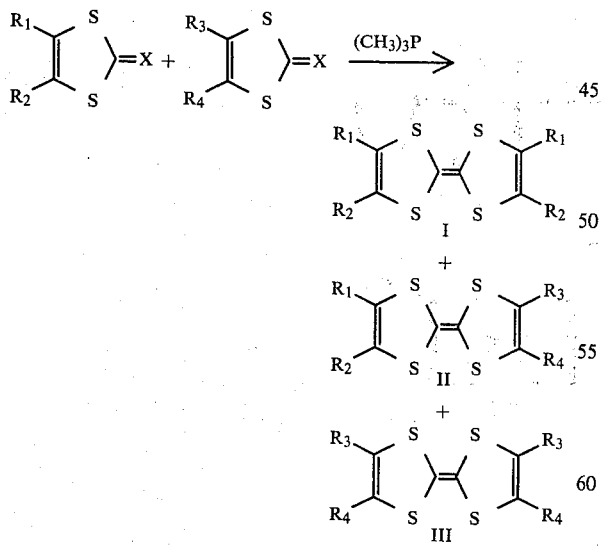

where $R_1$, $R_2$, $R_3$ and $R_4$ are selected from various organic groups such as alkyls, aryls, esters, sulfur containing compounds and the like. This method of synthesis, however, has its obvious drawbacks, in that there are three possible products, which are most difficult to separate. For cross coupling reactions multi-step procedures are sometimes required to obtain just one of the components to be coupled. The variety of substituents that can be substituted is severely limited to reagents that will not react with the coupling reagents. Narita et al further discloses tetra carboxy substituted tetrathiafulvalenes from which the dicarboxy substituted heterothiafulvalenes are formed by decarboxylation. Notably, the reference does not teach or suggest a mono carboxy substituted tetrathiafulvalene. This is probably due to the fact that the decarboxylation reaction for the mono carboxy reaction is so much faster than for the dicarboxy reaction, that it, the mono carboxy product is not formed or at best only transitory, thus never isolated. Attempted substitution of TTF by direct action of a reagent such as a halogen has been shown to yield not the substituted derivative, but rather the unsubstituted radical cation salt. (F. Wudl et al, *JCS Chem. Commun.* 1970, 1453). This points up the difference between the chemistry of TTF and other sulfur heterocycles such as thiophene TTF. Thiophene is related to TTF in that they both have the C—S—C=C linkage in common. However, while direct substitution can be made to thiophene by a number of methods (F. F. Blicke, Heterocyclic Compounds, John Wiley & Sons, N. Y. pg. 208), it appears that the only substitution common to both TTF and thiophene is that of lithiation and subsequent reaction thereof.

In summary; prior art attempts to prepare unsymmetrically substituted TTF or TSeF derivatives have used mixed coupling reactions that give multi-product mixtures that are difficult to separate and which yield only a limited variety of substituents. Direct substitution methods have resulted in oxidative attack on the central double bond and have yielded only radical cation salts.

It has been discovered here that substituted fulvalene compounds can be synthesized through a metal organic fulvalene lithium compound. It is likely that sodium or other alkali metals would function as well. The synthesis using the fulvalene lithium can be reacted in most cases in one step to form the desired substituted fulvalene compound. Additional derivatives can then be obtained if desired via further reactions. The present method has the advantages over the cross coupling method in that it is shorter, more direct, versatile and requires fewer starting materials.

SUMMARY OF THE INVENTION

In accordance with the invention there is provided novel TTF, TSeF and DTDSeF derivatives, their conducting salts with TCNQ and a novel method for their preparation.

Generally the method can be characterized by the steps of:

1. forming a fulvalene lithium compound and
2. reacting said fulvalene lithium compound with a reagent selected from the group consisting of $CO_2$, R R'C=O, RCHO, RC≡N, RX, $X_2$, ($CH_3I$ plus S), $SO_2$, CuCl, $(RO)_2SO_2$, $R_3SnCl$, $R_3$ Si Cl, HCHO, $ClCO_2R$, RCOCl, DMF,

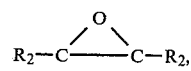

$R_3O^+PF_6^-$ where R and R' can be alkyl, aryl, alkenyl, heterocyclic or H, and X is a halogen, to obtain the desired corresponding product.

Accordingly, it is an important aspect of this invention to provide substituted fulvalene compounds. It is another object of this invention to provide a method of synthesis of substituted fulvalene derivatives wherein a fulvalene-lithium metal compound is formed as a stable compound at low temperatures. It is still a further object of the invention to provide substituted fulvalenes and their electrically conducting salts.

The foregoing and other objects, features and advantages of the invention will become more apparent from the following more particular description of the preferred embodiments.

PREFERRED EMBODIMENTS

In accordance with the invention there is provided novel substituted fulvalene compounds and a novel method for the synthesis thereof.

The synthesis includes the step of alkali metal metallation of a fulvalene selected from TTF, TSeF and DTDSeF. The fulvalene alkali metal compound can then be reacted with a host of other organic compounds. The following scheme is illustrative of the many novel substituted fulvalene compounds that become available by the method of this invention. It should be noted that while lithium is used to illustrate the invention, other alkali metals such as sodium and potassium is also contemplated for use herein Unlike the multi-substituted compounds obtained by the aforementioned coupling reaction, the compounds obtained by the present method produce heretofore unknown unsymmetrical derivatives of fulvalenes. Multi-substituted fulvalenes can be prepared according to the following reaction:

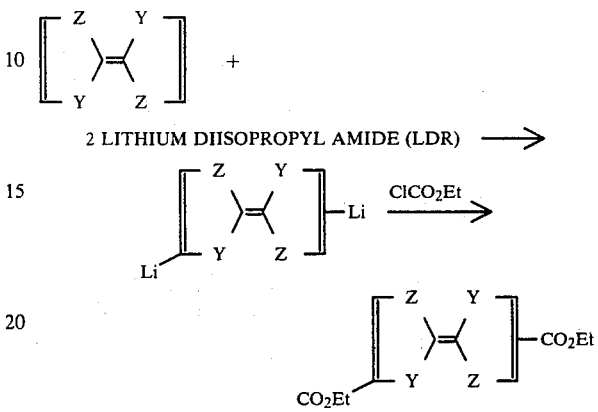

where Z is S and Y is S, Z is Se and Y is Se, and Z is S and Y is Se (Cis and trans isomers).

Alternatively, the above reaction can be carried out

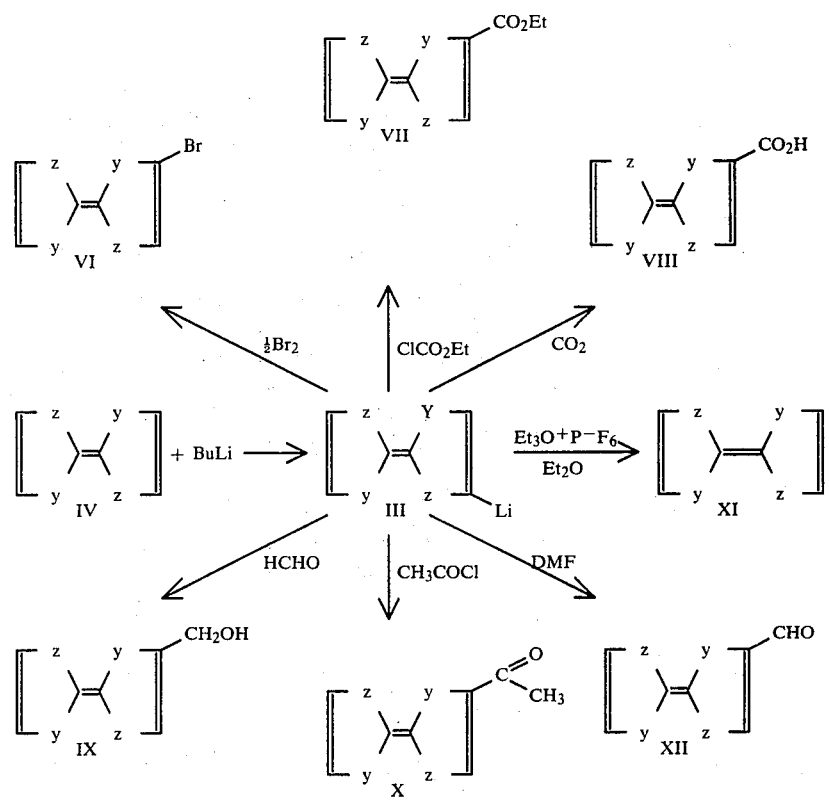

where
Z is S and Y is S,
Z is S and Y is Se,
Z is Se and Y is Se,
and it is understood that when Z is S and Y is Se that two isomers exist.

In addition, to the hitherto unknown monosubstituted derivatives obtained above, multi-substituted derivatives can also be synthesized by the present method.

sequentially because LDA metallations can be affected in the presence of the $CO_2H$ or $CO_2R$ groups without side reactions. For example

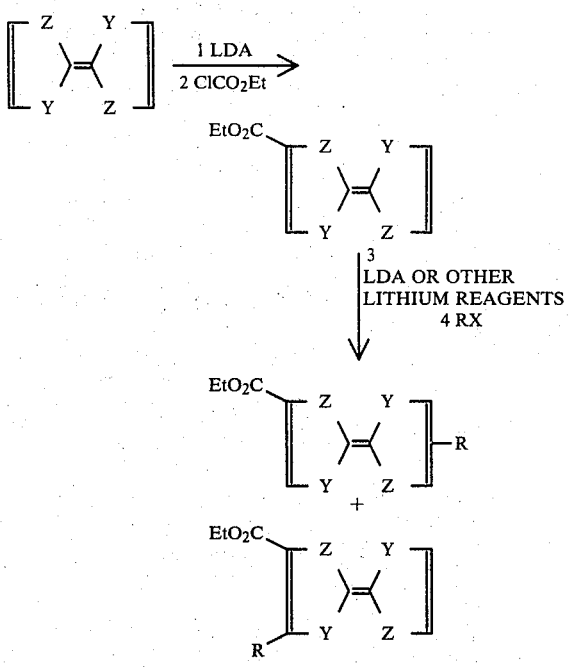

where Z is S and Y is S, Z is Se and Y is Se, and Z is S and Y is Se (Cis and trans isomers).

The substituted fulvalenes can be used to form charge-transfer salts with TCNQ. These charge-transfer compounds are now finding numerous electrolytic and semiconductor applications such as use in capacitors, conductive films, antistatic agents and the like. The substituted compositions of the present invention can be coupled to polymers to thereby provide electrically conducting or semiconducting polymers. These polymers are useful in integrated circuits and solid electrolytic condensers. The utility of these compositions are disclosed in the following Japanese patents 75-52, 594, 73-37,569, 75-27,098, 74-16,895, 75-56,593 and 74-54,484.

Lithium compositions used for lithiation in the present invention can be selected from any of a number of commercially available compounds, such as butyl lithium, phenyllithium, ethyllithium and lithium diisopropyl amide (LDA). The lithium compound is usually in an ethereal or hydrocarbon solution and is of a reagent grade. LDA however, is purchased as a solid. Sodium or other alkali metals are expected to function similarly although lithium is generally preferred for ease in handling.

The fulvalene compounds are prepared according to known methods. For example, several schemes for their preparation and given in the publication entitled Preparation of Tetrathiafulvalene (TTF) and their Selenium Analogs-Tetraselenafulvalenes (TSeF), by Mitsuaki Narita et al, Synthesis, pp. 489-514, August 1976.

All reactions in the present invention are carried out in an atmosphere other than $O_2$. The atmosphere can be $N_2$ or an inert gas such as argon.

The lithiated fulvalenes formed in the present invention because of their instability at elevated temperatures are not isolated and are not characterized in the usual manner. They are used in solution and are unambiguously characterized by the products formed therefrom. The lithiated fulvalenes are generally reacted with the desired reagent at a temperature of from about $-40°$ C. to about $-80°$ C.

The following is a list of general reactions contemplated by the present invention. These reactions are similar to those known for other organolithium reactions. See J. M. Mullan et al, Chemical Reviews, 69, 693-755, (1969).

It should be noted that RLi is the lithium compound of TTF, TSeF or DTDSeF, R' and R" can be different or be equal to each other and can be selected from alkyl, aryl, alkenyl, heterocylic and ether substituted alkyl groups. X is a halogen selected from Cl, Br and I.

| Fulvalene Lithium Comp. + Reactant | Product |
|---|---|
| $RLi + CO_2$ | → $RCO_2H$ |
| $RLi + R'R''C=O$ | → $RR'R'''COH$ |
| $RLi + R'CHO$ | → $RR'CHOH$ |
| $RLi + R'C\equiv N$ | → $RCOR'$ |
| $RLi + R'X$ | → $RR'$ |
| $RLi + X_2$ | → $RX$ |
| $RLi + R'X+S$ | → $RSR'$ |
| $RLi + SO_2$ | → $RSO_2Li+$ |
| $2RLi + CuCl$ | → $R-R$ |
| $RLi + (R'O)_2SO_2$ | → $R-R'$ |
| $RLi + CuBr$ | → $R-Cu$ |
| $RLi + R_3'SnCl$ | → $RSnR_3'$ |
| $RLi + R_3'SiCl$ | → $RSiR_3'$ |
| $RLi + HCHO$ | → $RCH_2OH$ |
| $RLi + ClCO_2R'$ | → $RCO_2R'$ |
| $RLi + R'CO_2R''$ | → $RR'CHOH$ |
| $RLi + DMF$ | → $RCHO$ |
| $RLi + R_2'C\overset{O}{\underset{}{-\!-\!-}}CR_2'$ | → $RCR_2'CR_2'OH$ |
| $RLi + H_2O$ | → $RH$ |
| $RLi + D_2O$ | → $RD$ |
| $RLi + R_3'O^+PF_6^-$ | → $RR'$ |

EXAMPLES

The following examples are by way of illustration and is in no manner restrictive of the present invention.

EXAMPLE 1

Preparation of monocarboxylic acid of TTF (TTF-$CO_2H$) and its methylester (TTFCO$_2$Me) —Method 1.

A quantity of TTF 1 gram (0.0049 mole) is dissolved in 100 ml of dried diethyl ether in a flask dried and purged with nitrogen. A solution of 1.96 M butyl lithium is hexane (2.5 ml, 0.0049 mole) is added dropwise into the TTF solution with stirring for period of about 15 minutes and at a temperature of about 25° C. The solution is further stirred for about 30 minutes and then poured onto a large excess of solid carbon dioxide (dry ice). After a 30 minute period, the reaction mixture is allowed to warm to about room temperature. Diethyl ether is then added and the solution extracted with 5% NaOH solution. Unreacted TTF is removed in the etheral layer. The aqueous layer is acidified with 10% HCl and extracted with ether. The ether solution is dried and evaporated to yield 0.1 g of a red solid (% yield=8%) the product has a melting point of about 176° to about 178° C. with decomposition.

Esterification of the acid is carried out by dissolving the solid in methanol and refluxing the solution to which 2 drops of concentrated $H_2SO_4$ has been added, for 16 hours.

NMR of the Ester gave 1 proton $\delta=7.4$ (singlet), 2 protons $\delta=6.3$ (singlet) and 3 protons $\delta=3.8$ (singlet) relative to tetramethylsilane (TMS). TTF $CO_2H$ infrared spectrum C=O stretch 1660 cm$^{-1}$ TTF CO$_2$Me infrared spectrum C=O stretch 1720 cm$^{-1}$.

EXAMPLE 2

Preparation of Monocarboxylic Acid of TTF (TTFCO$_2$H)—Method 2

A reaction flask containing 1.02 gram (0.005 mole) of TTF dissolved in 50 ml of ether is placed in a dry box under an argon atmosphere. The reaction flask is fitted with a thermometer, magnetic stirring bar, an addition funnel and a rubber syringe cap. Lithium diisopropylamide (LDA) (5.35 grams-0.005 mole) is dissolved in 10 ml of ether and added to the addition funnel. The flask is stoppered and brought outside of the dry box and purged with nitrogen. The TTF solution is cooled to about −50° C. with a dry ice acetone external bath. The LDA solution is added dropwise for about 15 minutes at about −50° C. to about −60° C. with stirring. The mixture is then stirred for an additional 30 minutes. The slurry in the reaction flask is then pressed over through a teflon tube (by applying nitrogen pressure) into a flask containing dry ice. The dry ice and solvent is allowed to evaporate after which a weak sodium hydroxide solution is added to the resultant red solid residue. The mixture is filtered to recover unreacted TTF. The filtrate is then acidified with a 5% hydrogen chloride solution and the resulting red precipitate is collected on a filter and dried under vacuum to yield 0.78 (57% yield). The precipitate is recrystallized from chloroform to obtain 0.5 grams of red needles having a melting point of about 182° C. to about 184° C. An infrared spectrum of the product via KBr pellet indicate the carbonyl group stretch to appear at 1660 cm$^{-1}$. The NMR analysis in D$_6$ acetone indicated 1 proton δ=7.6 (singlet, 2 protons δ=6.7 (singlet), 1 proton (CO$_2$H) δ=4.7 (singlet), (CO$_2$H proton moves to δ 5.35 in benzene D$_6$). This disappears with the addition of D$_2$O to the example. Elemental analysis C$_7$H$_4$O$_2$S$_2$

| Element | % Found | Theory % |
|---------|---------|----------|
| C | 34.03 | 33.85 |
| H | 1.50 | 1.62 |
| O | 13.03 | 12.89 |
| S | 51.18 | 51.64 |

Mass spectrum parent peak 248 AMU.

Electrochemical Data; 2 reversible waves. E$_1$ Peak= +0.475v vs saturated calomel electrode (SCE); E$_2$ Peak= +0.385 v vs SCE; 0.1 M tetraethylammonium perchlorate (TEAP) CH$_3$CN; 0.2v/sec scan rate; Pt electrode. The neutral state ester is deep red. Upon electrochemical oxidation the color changes to brownish black. The red color can be regenerated by electrochemical reduction, that is:

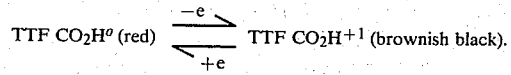

This property makes this material and those shown in subsequent examples useful as electrochromic materials for display applications.

EXAMPLE 3

Preparation of ethyl ester of TTF (TTFCO$_2$Et) lithium TTF is prepared according to the method disclosed in Example 2. To a solution of lithium TTF (0.0049 mole) maintained at a temperature of about −70° C. is added a 5 fold excess (0.27 grams) of ethylchloroformate (ClCO$_2$Et). The mixture is stirred, slowly warmed to about room temperature, added to water and extracted with ether. The ether layer is then separated and dried over MgSO$_4$. The ether and ethylchloroformate are removed under vacuum. A crystalline compound having a melting point of about 79.5° C. to about 80.5° C. (uncorrected) is obtained. The IR spectrum indicated the carbonyl group stretch to appear at 1690 cm$^{-1}$ (KBr). The NMR analysis indicated 1 proton δ=7.3 singlet (methine), 2 protons δ=6.3 singlet (methine); 3 protons δ=4.25 (methylene) J=7 Hz: 3 protons δ=1.35 triplet (methyl) J=7 Hz. The color is light red

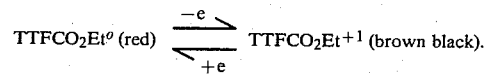

Electrochemical data: 2 reversible oxidation waves E$_{1peak}$= +0.47V; E$_{2peak}$= +0.83V vs. SCE 0.1 m TEAP/CH$_3$CN 0.2 volts/sec scan. rate, Pt electrode.

EXAMPLE 4

Preparation of Ethyl TTF

Lithium TTF (0.0049 mole) is prepared according to Example 2. The lithium TTF solution is maintained at a temperature of about −70° C. and is added to a flask containing 1.36 grams (Et$_3$O$^+$ $^-$PF$_6$) (0.0055 mole) in 25 ml of ether by pressing through a Teflon tube using nitrogen pressure. The mixture is stirred for about 1 hour and then brought slowly to about room temperature. It is then added to water and extracted with ether. The ether layer is separated, dried over MgSO$_4$, and evaporated. The product is separated from unreacted TTF using dry column chromatography with a 1.25 inch by 24 inch column of neutral grade 3 alumina with hexane as the eluent. The product which is a yellow band is cut out and again chromatographed to yield 0.1 grams of a yellow oil which does not crystallize at room temperature. NMR analysis in CCl$_4$ relative to TMS gave 2 protons δ=7.3 singlet (methine); 1 proton δ=5.8 singlet (methine); 2 protons δ=2.45 (methylene) quartet J=8 Hz; 3 protons δ1.25 (methyl) triplet J=7 Hz. The infrared spectral analysis indicated the following major peaks at 3070, 2970, 2930, 1450, 820, 795, 780, 735, and 645 cm$^{-1}$. The electrochemical data indicate 2 reversible oxidation waves E$_{1peak}$= +0.33 volts; E$_{2peak}$= +0.70 volts vs. SCE; 0.2 m TEAP CH$_3$CN; platinum electrode 0.2V/sec. scan rate.

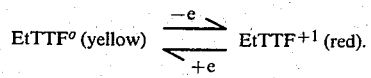

EXAMPLE 5

Preparation of TTFCOCH$_3$ (TTF Methyl ketone)

Lithium TTF (0.005 mole) is prepared according to Example 2 and is prepared at −70° C.

The lithium TTF solution is added to a five fold molar excess solution (2 g) of CH$_3$COCl in ether at −70° C. with stirring. After the addition is completed the mixture is warmed for about 1 hour to about room temperature. The ether and excess acetylchloride is removed under vacuum. The resultant solid is dissolved in benzene and the LiCl is removed by filration. The mixture is purified by dry column chromatography on a silica gel (grade III) column (4.5×10 cm) by first eluting with hexane to remove unreacted TTF and then with benzene to remove the product band from the column. Deep red crystals are obtained with a melting point of about 152° C. to about 153° C. (uncorrected) A 67% yield (0.08 g) is obtained.

NMR δ=7.32 1 proton (methine) singlet, 67 =6.35 2 protons (methine) singlet, δ=2.40 3 protons (methyl) singlet.

IR spectrum shows the carbonyl stretch at 1635 cm$^{-1}$ (KBr Pellet).

Electrochemical data $E_{1Peak}$= +0.47V vs. SCE; $E_{2Peak}$= +0.83V vs. SCE.

Pt electrode; 0.1 M TEAP/CH$_3$CN; scan rate 0.2V/sec.

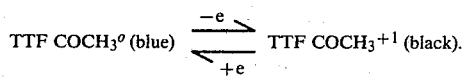

EXAMPLE 6
Preparation of TSeFCO$_2$H

Lithium TSeF and TSeFCO$_2$H are prepared exactly according to the procedure for the preparation of TTFCO$_2$H in Example 2, except that TSeF 100 mg, (0.00026 mole) and LDA 28 mg (0.00026 mole) are used. A yield of 13 mg of TSeFCO$_2$H is obtained. Melting point: The product decomposed at about 165° C. before melting.

Electrochemical Data:2 reversible waves
Pt electrode:Ep= +0.63V vs. SCE
CH$_3$CN/0.1 M TEAP:Ep= +0.90V vs. SCE
Scan rate 0.2 V. sec.

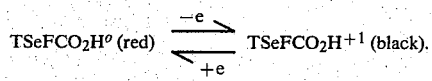

IR spectrum indicated that the carbonyl peak appears at 1670 cm$^{-1}$.

EXAMPLE 7
Preparation of TTF CHO

TTF Li (0.0049 mole) is prepared according to method 2 at −70° C. This was added at −70° C. to a stirred solution of ether containing a five fold molar excess of N,N-dimethylformamide (DMF) at −70° C. The mixture is allowed to come to room temperature and then added to water (which had been purged with N$_2$ to remove O$_2$). This is extracted with ether. The ether layer is dried and the ether removed under vacuum. The mixture is purified by dry column chromatography on a silica gel (grade III) column (4.5×8 cm) by first eluting with hexane to remove unreacted TTF and then with benzene to isolate the product. Deep red crystals (0.58 g 44% yield) are obtained having a melting point of about 98 to about 99° C. (uncorrected).

IR spectrum indicated that the aldehydic carbonyl appears at 2810 cm$^{-1}$ and 1660 cm$^{-1}$.

NMR δ=9.52 (aldehydic) 1 proton, δ=7.48 (methine) 1 proton, δ=6.38 (methine) 2 protons.

Electrochemical data: 2 reversible waves
0.1 M TEAP/CH$_3$CN:$E_{1Peak}$= +0.53 V vs. SCE
0.2 V/sec scan rate
Pt electrode:$E_{2Peak}$= +0.89 V vs. SCE

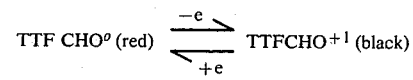

EXAMPLE 8
Preparation of Vinyl TTF (ViTTF)

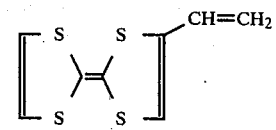

A slurry of φ$_3$P⊕CH$_3$B⊖r (0.39 g, 0.0011 mole) in 25 ml of dry ether is prepared under nitrogen. To this is added dropwise at 22° C., 0.61 ml of 1.8 M BuLi in 10 ml of ether over a 10 min. period. The resulting orange solution was stirred for 1 hr. Then 0.25 g (0.001 mole) of TTFCHO in 30 ml of ether was added dropwise over 10 min. A white-tan precipitate separated. The mixture is stirred for 1 hr. and the precipitate (φ$_3$PO and LiCl) is filtered off. The ether solution is evaporated under vacuum and the residue is purified by dry column chromatography using Grade III silica gel. The product is eluted from the impurities with hexane. There is obtained 0.1 g (39% yield) of a bright yellow oil

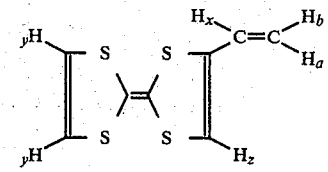

$H_x$ 1 proton Quartet δ=6.38 $J_{bx}$=17 Hz $j_{ax}$=11 Hz
$H_a$ 1 proton Doublet δ=5.11 $J_{ax}$=11 Hz
$H_b$ 1 proton Doublet δ=5.03 $J_{bx}$=17 Hz
$H_y$ =Hz 3 protons (coincidently) δ=6.07(singlet)
IR spectrum indicates that the C═C stretch appears at 1610 cm$^{-1}$, other IR peaks occur at 3070(S), 2960(W), 2920(M), 1800(W), 1610(S), 1532(S), 1415(W), 1290(W), 1258(W), 1240(M), 1150(S), 1095(M), 973(S), 902(S), 829(S) 800(S), 780(S), 770(S), 740(M), 645(S) cm$^{-1}$.

Electrochemical Data:2 reversible waves
0.1 M TEAP/CH$_3$CN:$E_{1Peak}$= +0.415 V vs. SCE
0.2 V/sec Scan rate:$E_{2Peak}$= +0.770 V vs. SCE

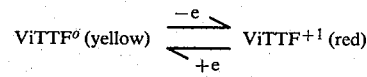

Pt electrode

EXAMPLE 9
Preparation of TTFCO$_2$H-TCNQ

Equimolar portions of TTFCO$_2$H and TCNQ are mixed in CH$_3$CN. After several minutes a black precipitate separates and is collected on a filter. The crystals are compressed into a pellet which shows a conductivity of 8.3 ohm$^{-1}$ cm$^{-1}$ at 25° C.

EXAMPLE 10

Preparation of Ethyl TTF TCNQ

Equimolar portions of ETTF and TCNQ are mixed in $CH_3CN$. The resulting black precipitate shows a resistance when pressed between the electrodes of an ohm-meter of 40 ohms.

Similarly, monosubstituted derivatives of DTDSeF can also be prepared. The chemistry and physical properties of DTDSeF are known to be akin to TTF and TSeF compounds as shown in U.S. Pat. No. 4,028,346 to Engler et al.

The compositions of this invention are useful as organic conductors and semiconductors in the form of their charge transfer salts with suitable electron acceptors such as TCNQ as indicated above. Additionally they are also useful in such applications as optical printing and electrochromic display devices as demonstrated in U.S. Pat. Nos. 4,036,648, 4,082,552 and in the publication to B. A. Scott et al, entitled Formation of Highly Conducting Organic Salts by Photooxidation of Heterofulvalene π-Donors in Halocarbon Solutions.

As an example of their use in optical processes as described in the above-mentioned patents and publication, a solution containing 1 mg/ml of $TTFCO_2H$ in $CCl_4$ was prepared and stored in the dark. A aliquot of 0.5 ml of this solution is applied to a 10 m² area of ordinary typing paper and covered with a mask. The mask is then illuminated with low intensity (0.5 watts/cm²) ultraviolet radiation at 3650A for one minute, removed, and the excess $CCl_4$ allowed to evaporate. A brown black conducting image was deposited on the paper. Similar images are obtained when other materials of this invention are treated in like manner.

The wide variety of TTF derivatives now made available by the present invention will now provide a wide range of color variation. For example, the introduction of electron withdrawing chromophores will increase the intensity of the effect. The monosubstituted derivatives described herein have the added advantage that they are of sufficiently low ionization potentials to form charge transfer complexes.

the compositions of the present invention can be used in electrochromic display devices, because they exhibit two electrochemically reversible waves and have very intensely colored states in their +1 oxidized forms as indicated in the above examples.

The invention has been described in detail with particular reference to certain preferred embodiments thereof, but it will be understood that variations and modifications can be effected within the spirit and scope of the invention.

Having thus described my invention, what I claim as new, and desire to secure by Letters Patent is:

1. Substituted tetrathiafulvalenes, tetraselenafulvalenes and dithiadiselenafulvalenes having the formulae

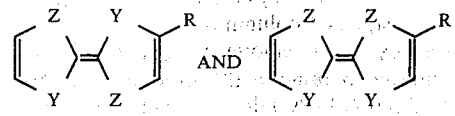

where Z and Y is S, Z is S and Y is Se, and Z is Se and Y is Se, and R is a substituted selected from the group consisting of: $-CO_2H$, $-CO_2C_2H_5$, $-COCH_3$, $-CHO$, $-Cl$, $-Br$, $-I$, $-CH=CH_2$ $-CO_2CH_3$, $CH_2-CH_3$ and $-CH_2OH$.

2. Compositions of matter according to claim 1 wherein Z is S and Y is S and R is selected from the group consisting of $-CO_2H$, $-CO_2C_2H_5$, $-CH_2CH_3$, $-COCH_3$, $-CHO$, $-CH=CH_2$ and $-CO_2CH_3$.

3. A composition of matter according to claim 1 wherein Z is S and Y is Se.

4. A composition of matter according to claim 1 wherein Y is Se and Z is Se.

5. A composition of matter according to claim 1 wherein Y is S and Z is Se.

6. Compositions of matter having the general formulae

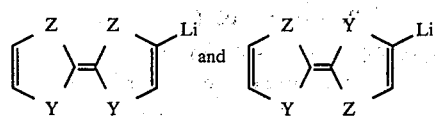

where Y is selected from the group consisting of S and Se and Z is selected from the group consisting of S and Se.

7. A composition of matter according to claim 6 wherein Y is S and Z is S.

8. A composition of matter according to claim 6 wherein Y is Se and Z is Se.

9. As a composition of matter the TCNQ salts of substituted derivates of tetrathiafulvalene, tetraselenafulvalenes and dithiadiselenafulvalene having the formulae

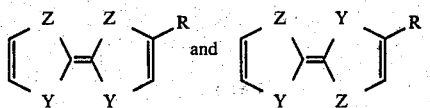

where Z is S and Y is S, Z is S and Y is Se, and Z is Se and Y is Se, and where R is selected from the group consisting of $-CO_2H$, $-CO_2C_2H_5$, $-COCH_3$, $-CHO$, $-Cl$, $-Br$, $-I$, $-CH_2=CH_3$, $-CH_2OH$, $-CH=CH_2$ and $-CO_2CH_3$.

10. A composition of matter according to claim 9 wherein R is selected from the group consisting of $-CO_2H$, $-CO_2C_2H_5$, $-CH_2CH_3$, $-COCH_3$, $-CHO$, $CH=CH_2$, and $CO_2CH_3$.

11. A composition of matter according to claim 9 wherein Z is S and Y is S.

12. A composition of matter according to claim 9 wherein Z is Se and Y is Se.

13. A composition of matter according to claim 9 wherein Z is S and Y is Se.

14. A composition of matter according to claim 4 wherein R is $CO_2H$.

15. A composition of matter according to claim 9 wherein Z is S and Y is S and where R is selected from the group $-CO_2H$ and $-CH_2CH_3$.

* * * * *